(12) United States Patent
Allison

(10) Patent No.: US 10,888,366 B2
(45) Date of Patent: Jan. 12, 2021

(54) CRYOGENIC BLUNT DISSECTION METHODS AND DEVICES

(71) Applicant: Pacira CryoTech, Inc., Parsippany, NJ (US)

(72) Inventor: John Allison, Los Altos, CA (US)

(73) Assignee: Pacira CryoTech, Inc., Parsippany, NJ (US)

( * ) Notice: Subject to any disclaimer, the term of this patent is extended or adjusted under 35 U.S.C. 154(b) by 520 days.

(21) Appl. No.: 15/893,178

(22) Filed: Feb. 9, 2018

(65) Prior Publication Data

US 2018/0168709 A1   Jun. 21, 2018

Related U.S. Application Data

(63) Continuation of application No. 14/218,886, filed on Mar. 18, 2014, now abandoned.
(Continued)

(51) Int. Cl.
   *A61B 18/02*   (2006.01)
   *A61F 7/00*    (2006.01)
   *A61B 18/00*   (2006.01)

(52) U.S. Cl.
   CPC ............ *A61B 18/02* (2013.01); *A61F 7/00* (2013.01); *A61B 2018/00023* (2013.01);
   (Continued)

(58) Field of Classification Search
   CPC .......... A61B 18/02; A61B 2018/00023; A61B 2018/00321; A61B 2018/00434;
   (Continued)

(56) References Cited

U.S. PATENT DOCUMENTS 2,319,542 A   5/1943   Hall
2,672,032 A   3/1964   Towse
(Continued)

FOREIGN PATENT DOCUMENTS

CA   2643474   9/2007
EP   0043447   1/1982
(Continued)

OTHER PUBLICATIONS

Advanced Cosmetic Intervention, Inc., http://www.acisurgery.com, 2007, 1 page.
(Continued)

*Primary Examiner* — Daniel W Fowler
(74) *Attorney, Agent, or Firm* — Kilpatrick Townsend & Stockton LLP

(57) ABSTRACT

A point of incision is created within tissue, the tissue having a temporoparietal fascia-deep temporoparietal fascia layer (TPF-sDTF) beneath skin and a temporal branch of a target nerve extending along a portion of the TPF-sDTF, the point of incision being laterally displaced from the target nerve. A cryogenic probe having a distal tip extending from an elongated body is inserted into the point of incision. The TPF-sDTF is bluntly dissected using the cryogenic probe such that a treating portion of the cryogenic probe is directly adjacent to a first treatment portion of the target nerve. The cryogenic probe is activated to create a first treatment zone at the first treatment portion of the target nerve to cause a therapeutic effect.

35 Claims, 14 Drawing Sheets

Related U.S. Application Data

(60) Provisional application No. 61/801,268, filed on Mar. 15, 2013.

(52) U.S. Cl.
CPC ............... *A61B 2018/00321* (2013.01); *A61B 2018/00434* (2013.01); *A61B 2018/00452* (2013.01); *A61B 2018/0262* (2013.01); *A61B 2018/0293* (2013.01)

(58) Field of Classification Search
CPC .. A61B 2018/00452; A61B 2018/0262; A61B 2018/0293
See application file for complete search history.

(56) References Cited

U.S. PATENT DOCUMENTS

| | | |
|---|---|---|
| 3,266,492 A | 8/1966 | Steinberg |
| 3,289,424 A | 12/1966 | Shepherd |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,910,278 A | 10/1975 | Crandell |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A | 8/1990 | Merry et al. |
| 5,059,197 A | 10/1991 | Urie et al. |
| 5,200,170 A | 4/1993 | McDow |
| 5,201,729 A | 4/1993 | Hertzmann et al. |
| 5,294,325 A | 3/1994 | Liu |
| 5,334,181 A | 8/1994 | Rubinsky et al. |
| 5,417,689 A | 5/1995 | Fine |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,759,182 A | 6/1998 | Varney et al. |
| 5,814,040 A | 9/1998 | Nelson et al. |
| 5,860,970 A | 1/1999 | Goddard et al. |
| 5,879,378 A | 3/1999 | Usui |
| 5,899,897 A | 5/1999 | Rabin et al. |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 | 2/2001 | Dobak, III |
| 6,193,672 B1 | 2/2001 | Clement |
| 6,196,839 B1 | 3/2001 | Ross |
| 6,238,386 B1 | 5/2001 | Müller et al. |
| 6,277,099 B1 | 8/2001 | Strowe et al. |
| 6,277,116 B1 | 8/2001 | Utely et al. |
| 6,363,730 B1 | 4/2002 | Thomas et al. |
| 6,371,943 B1 | 4/2002 | Racz et al. |
| 6,432,102 B2 | 8/2002 | Joye et al. |
| 6,494,844 B1 | 12/2002 | Van Bladel et al. |
| 6,503,246 B1 | 1/2003 | Har-shai et al. |
| 6,506,796 B1 | 1/2003 | Fesus et al. |
| 6,546,935 B2 | 4/2003 | Hooven |
| 6,551,309 B1 | 4/2003 | Lepivert |
| 6,562,021 B1 | 5/2003 | Derbin et al. |
| 6,562,030 B1 | 5/2003 | Abboud et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,902,554 B2 | 6/2005 | Huttner |
| 6,905,492 B2 | 6/2005 | Zvuloni et al. |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,195,616 B2 | 3/2007 | Diller et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 | 8/2009 | Bleich et al. |
| 7,641,679 B2 | 1/2010 | Joye et al. |
| 7,713,266 B2 | 5/2010 | Elkins et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,715,275 B2 | 5/2014 | Burger et al. |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0087208 A1 | 7/2002 | Koblish et al. |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0181896 A1 | 9/2003 | Zvuloni et al. |
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |

(56) References Cited

U.S. PATENT DOCUMENTS

| | | |
|---|---|---|
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0059964 A1 | 3/2005 | Fitz |
| 2005/0065504 A1 | 3/2005 | Melsky et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0222558 A1 | 10/2005 | Baxter et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0030845 A1 | 2/2006 | Leung et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0095059 A1 | 5/2006 | Bleich et al. |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0049924 A1 | 3/2007 | Rahn |
| 2007/0055173 A1 | 3/2007 | Delonzor et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179340 A1 | 8/2007 | Jorgensen |
| 2007/0179509 A1 | 8/2007 | Nagata et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0033415 A1 | 2/2008 | Rieker et al. |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0036823 A1 | 2/2009 | Lepivert |
| 2009/0118722 A1 | 5/2009 | Ebbers et al. |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299357 A1 | 12/2009 | Zhou |
| 2010/0016847 A1 | 1/2010 | Fischer et al. |
| 2010/0241114 A1 | 9/2010 | Privitera et al. |
| 2011/0144631 A1 | 6/2011 | Elkins et al. |
| 2012/0065629 A1 | 3/2012 | Elkins et al. |
| 2012/0089211 A1 | 4/2012 | Curtis et al. |
| 2012/0265187 A1 | 10/2012 | Palmer, III et al. |
| 2013/0324990 A1 | 12/2013 | Burger et al. |
| 2014/0249519 A1 | 9/2014 | Burger et al. |
| 2014/0350536 A1 | 11/2014 | Allison |

FOREIGN PATENT DOCUMENTS

| | | |
|---|---|---|
| EP | 777123 | 6/1997 |
| EP | 955012 | 11/1999 |
| EP | 1074273 | 2/2001 |
| EP | 1377327 | 9/2007 |
| EP | 1862125 | 12/2007 |
| GB | 1360353 | 7/1974 |
| GB | 1402632 | 8/1975 |
| JP | 60013111 | 1/1985 |
| JP | 04357945 | 12/1992 |
| JP | 05038347 | 2/1993 |
| JP | 10014656 | 1/1998 |
| JP | 2001178737 | 7/2001 |
| JP | 2005080988 | 3/2005 |
| JP | 2006130055 | 5/2006 |
| JP | 2008515469 | 5/2008 |
| RU | 2254060 | 6/2005 |
| WO | 9749344 | 12/1997 |
| WO | 0197702 | 12/2001 |
| WO | 0202026 | 1/2002 |
| WO | 02092153 | 11/2002 |
| WO | 2004039440 | 5/2004 |
| WO | 2004045434 | 6/2004 |
| WO | 2004089460 | 10/2004 |
| WO | 2005000106 | 1/2005 |
| WO | 2005079321 | 9/2005 |
| WO | 2005096979 | 10/2005 |
| WO | 2006012128 | 2/2006 |
| WO | 2006023348 | 3/2006 |
| WO | 2006044727 | 4/2006 |
| WO | 2006062788 | 6/2006 |
| WO | 2006125835 | 11/2006 |
| WO | 2006127467 | 11/2006 |
| WO | 2007025106 | 3/2007 |
| WO | 2007037326 | 4/2007 |
| WO | 2007089603 | 8/2007 |
| WO | 2007129121 | 11/2007 |
| WO | 2007135629 | 11/2007 |
| WO | 2009026471 | 2/2009 |
| WO | 2010075438 | 7/2010 |
| WO | 2010075448 | 7/2010 |
| WO | 2014146126 | 9/2014 |

OTHER PUBLICATIONS

CryoPen, LLC, "CyroPen, LLC Launches Revolutionary, State-of-the-Art Medical Device—The Dure of Cryosurgery in a Pend", Press Release, retrieved from the Internet: http://cryopen.com/press.htm, Apr. 27, 2006, pp. 1-3.

Cryopen, LLC., "The future of Cryosurgery at your fingertips", retrieved from the Internet: http://cryopen.com/, 2006-2008, 2 pages.

Dasiou-Plankida, "Fat injections for facial rejuvenation: 17 years experience in 1720 patients", Journal of Cosmetic Dermatology, vol. 2, No. 3-4, Oct. 22, 2004, pp. 119-125.

Foster et al., "Radiofrequency Ablation of Facial Nerve Branches Controlling Glabellar Frowning", Dermatol Surg, vol. 35, No. 12, Dec. 2009, pp. 1908-1917.

Har-Shai et al., "Effect of Skin Surface Temperature on Skin Pigmentation During Contact and Intralesional Cryosurgery of

(56) References Cited

OTHER PUBLICATIONS

Hypertrophic Scars and Kleoids", Journal of the European Academy of Dermatology and Venereology, vol. 21, No. 2, Feb. 2007, pp. 191-198.

Magalov et al., "Isothermal volume contours generated in a freezing gel by embedded cryo-needles with applications to cryo-surgery", Cryobiology, vol. 55, No. 2, Oct. 2007, pp. 127-137.

Metrum Cryoflex, "Cryoablation in Pain Management brochure", Medical Devices Manufacturer, 2012, 5 pages.

Metrum Cryoflex, "Cryosurgery probes and accessories catalogue", Contact probes catalogue, 2009, 25 pages.

One Med Group, LLC, "CryoProbeTM", [webpage] retrieved from the internet: http://www.onemedgroup.com/, Feb. 4, 2008, pp. 1-2.

Rewcastle et al., "A model for the time dependent three-dimensional thermal distribution within iceballs surrounding multiple cryoprobes", Medical Physics, vol. 28, No. 6, Jun. 2001, pp. 1125-1137.

Rutkove, "Effects of temperature on neuromuscular electrophysiology", Muscles and Nerves, vol. 24, Issue 7, Jun. 12, 2001, pp. 867-882.

Utley et al., "Radiofrequency ablation of the nerve to the corrugator muscle for elimination of glabellar furrowing", Archives of Facial Plastic Surgery, vol. 1, No. 1, Jan.-Mar. 1999, pp. 46-48.

Yang et al., "Apoptosis induced by cryo-injury in human colorectal cancer cells is associated with mitochondrial dysfunction", International Journal of Cancer, vol. 103, Issue 3, Jan. 2003, pp. 360-369.

CRYOGENIC BLUNT DISSECTION METHODS AND DEVICES

CROSS REFERENCES TO RELATED APPLICATIONS

The present application is a Continuation of U.S. application Ser. No. 14/218,886 filed Mar. 18, 2014; which claims the benefit of U.S. Provisional Application No. 61/801,268, filed on Mar. 15, 2013, all of which are incorporated by reference herein in their entirety.

BACKGROUND OF THE INVENTION

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. Other embodiments may find use for a wide range of medical indications, for example, such as pain management, movement disorders, surgical methods, and aesthetic treatments. Such embodiments can include the treatment of peripheral nerves positioned within a fascia, such as sensory and motor nerves The remodeling of the target tissue may achieve a desired change in its behavior or composition.

Therapeutic treatment of chronic or acute pain is among the most common reasons patients seek medical care. Chronic pain may be particularly disabling, and the cumulative economic impact of chronic pain is huge. A large portion of the population that is over the age of 65 may suffer from any of a variety of health issues which can predispose them to chronic or acute pain. An even greater portion of the nursing home population may suffer from chronic pain.

Current treatments for chronic pain may include pharmaceutical analgesics and electrical neurostimulation. While both these techniques may provide some level of relief, they can have significant drawbacks. For example, pharmaceuticals may have a wide range of systemic side effects, including gastrointestinal bleeding, interactions with other drugs, and the like. Opiod analgesics can be addictive, and may also of themselves be debilitating. The analgesic effects provided by pharmaceuticals may be relatively transient, making them cost-prohibitive for the aging population that suffers from chronic pain. While neurostimulators may be useful for specific applications, they generally involve surgical implantation, an expensive which carries its own risks, side effects, contraindications, on-going maintenance issues, and the like.

Chemodenervation and Neurolysis are other techniques for treating pain in which a nerve is damaged so that it can no longer transmit signals. The use of neurotoxins (such as botulinum toxin or BOTOX®) for Chemodenervation has received some support. Unfortunately, significant volumes of toxins may be used on a regular basis for effective Chemodenervation, and such use of toxins can have significant disadvantages. Neurolysis techniques may involve injections of phenol or ethyl alcohol or the use of energy to cause a thermal injury to the nerves such as via the application of radiofrequency ("RF") energy to achieve ablation, or the like. While several of these alternative neurolysis approaches may avoid systemic effects and/or prevent damage, additional improvements to neurolysis techniques would be desirable.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary enervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, improved medical devices, systems, and methods utilizing a cryogenic approach to treating the tissue have been proposed, particularly for treatment of wrinkles, fat, cellulite, and other cosmetic defects. These new techniques can provide an alternative visual appearance improvement mechanism which may replace and/or compliment known bioactive and other cosmetic therapies, ideally allowing patients to decrease or eliminate the injection of toxins and harmful cocktails while providing similar or improved cosmetic results. These new techniques are also promising because they may be performed percutaneously using only local or no anesthetic with minimal or no cutting of the skin, no need for suturing or other closure methods, no extensive bandaging, and limited or no bruising or other factors contributing to extended recovery or patient "down time." Additionally, cryogenic treatments are also desirable since they may be used in the treatment of other cosmetic and/or dermatological conditions (and potentially other target tissues), particularly where the treatments may be provided with greater accuracy and control, less collateral tissue injury and/or pain, and greater ease of use.

While these new cryogenic treatments are promising, careful control of temperature along the cryogenic probe is necessary in order to obtain desired results in the target treatment area as well as to avoid unwanted tissue injury (tissue blackening) in adjacent areas. Further, there are challenges associated accuracy in finding the appropriate depth of target tissue. Thus, it is desirable to implement devices and methods to mitigate such issues. Further, it would be advantageous to provide improved devices, systems, and methods for management of chronic and/or acute pain. Such improved techniques may avoid or decrease the systemic effects of toxin-based neurolysis and pharmaceutical approaches, while decreasing the invasiveness and/or collateral tissue damage of at least some known pain treatment techniques.

BRIEF SUMMARY OF THE INVENTION

Embodiments of the invention are related to blunt dissection devices for laterally traversing a layer beneath skin from an incision point and treating a portion of tissue laterally displaced from the incision point.

Embodiments of the invention relate to certain methods. For many methods, a point of incision is created within tissue. The tissue includes skin, a layer of soft tissue and a layer of resilient tissue. A cryogenic probe having a distal tip extending from an elongated body is inserted into the point of incision. The soft tissue is bluntly dissected using the cryogenic probe such that a treating portion of the cryogenic probe is directly adjacent to the resilient layer. The cryogenic probe is then advanced along the resilient layer. The cryogenic probe is then repeatedly moving and activating the treating portion of such that a plurality of treatment zones is created across a nerve adjacent to the resilient layer.

In many embodiments, the soft tissue layer is comprised of adipose tissue, muscle, and/or subcutaneous tissue.

In many embodiments, the layer of resilient tissue is a fascia layer.

In many embodiments, the layer of resilient tissue is cartilage, periosteum, or bone.

For many methods, a point of incision is created within tissue, the tissue comprising a temporoparietal fascia-deep temporoparietal fascia layer (TPF-sDTF) beneath skin and a temporal branch of a facial nerve (TB-FN) extending along a portion of the TPF-sDTF. The point of incision is laterally displaced from the TB-FN. A cryogenic probe having a distal tip extending from an elongated body is then inserted into the point of incision. The TPF-sDTF is then bluntly dissected using the cryogenic probe such that a treating portion of the cryogenic probe is directly adjacent to a first treatment portion of the TB-FN. The cryogenic probe can be activated to create a cooling treatment zone at the treatment portion of the TB-FN and thus cause a therapeutic effect. Alternatively, the cryogenic probe can also be repeatedly moved and activated at the treating portion of the cryogenic probe such that a plurality of treatment zones is created across the TB-FN.

In many embodiments, the elongated body is placed such that it traverses across the first treatment portion of the TB-FN.

In many embodiments, the cooling treatment zone emanates from a distinct portion of the elongated body.

In many embodiments, the distal tip is placed such that it is located at the first treatment portion of the TB-FN.

In many embodiments, the cooling treatment zone emanates from the distal tip.

In many embodiments, methods include relocating the treating portion of the cryogenic probe to a second treatment portion of the TB-FN, and activating the cryogenic probe to create a second cooling treatment zone at the second treatment portion of the TB-FN to further the therapeutic effect.

In many embodiments, the second treatment zone is adjacent to the first treatment zone.

In many embodiments, the second treatment zone overlaps with the first treatment zone.

In many embodiments, the first treatment portion is directly beneath a visible area of the skin, and wherein the incision is directly beneath a portion of scalp covered by hair Embodiments of the invention relate to certain devices. Such devices can include a cryogenic probe having a distal tip extending from an elongated body adapted to laterally traverse a temporoparietal fascia-deep temporoparietal fascia layer (TPF-sDTF) beneath skin to a temporal branch of a facial nerve (TB-FN) extending along a portion of the TPF-sDTF from a point of incision being laterally displaced from the TB-FN. The distal tip can be adapted to bluntly dissect the TPF-sDTF such that a treating portion of the cryogenic probe is directly adjacent to a first treatment portion of the TB-FN. The elongated body houses a fluid path for creating a cooling treatment zone at the treatment portion of the TB-FN to cause a therapeutic effect. However, use of these devices are not limited to the TPF-sDTF, since in many embodiments, such devices can be used to traverse along a tissue interface or fascia conforming to the interface plane by blunt dissection along the interface in order to position the treatment tip in a desired tissue plane. For any target peripheral nerve, there exist at least one tissue interface or fascia layer that can be used as an internal body surface for deflecting the flexible blunt tip device so it adheres to the internal body surface for preferred placement. For example, if the target nerve has a fascia layer immediately below it, then this fascia is an ideal candidate for deflecting the flexible blunt tip device into treatment position because it will help guide the treatment portion of the blunt tip device into position adjacent to the target nerve.

Embodiments of the invention relate to systems having a probe body, an elongated probe extending from the probe body and having a blunt distal tip. A cryogen supply tube extends within the elongated probe. The elongated probe and supply tube are configured to resiliently bend. For example, resiliently bend such that the blunt distal tip glides along the sDTF while dissecting the TPF.

In many embodiments, the elongated probe is 15 gauge or smaller in diameter.

In many embodiments, the elongated probe is 20-30 mm in diameter.

In many embodiments, the elongated probe is over 30 mm in length.

In many embodiments, the elongated probe is 30-150 mm in length.

In many embodiments, a first portion of the elongated probe and cryogen supply tube are configured to resiliently bend at an angle up to 120°. In further embodiments, a second portion of the elongated probe and cryogen supply tube are configured to resiliently bend to a lesser degree than the first portion.

In many embodiments, a coolant supply source coupled to the supply tube.

In many embodiments, the supply tube comprises a fused silica tube having a reinforcement portion.

In many embodiments, the flexibility of the elongated probe can vary from one end to the other end in a continuous or discrete segments. The advantage of this is to allow the leading portion of the elongated probe to be less flexible so insertion force can be translated to the tip more effectively. When the tip encounters resistance and a lateral force, it is the portion of the needle to bend adhering to this lateral force while the proximal portion of the elongated probe deflects less.

In many embodiments, the system includes a cannula curved to assist in directing the elongated probe into a desired tissue layer coincident with predetermined pathway.

DETAILED DESCRIPTION OF THE INVENTION

Figure 1A:
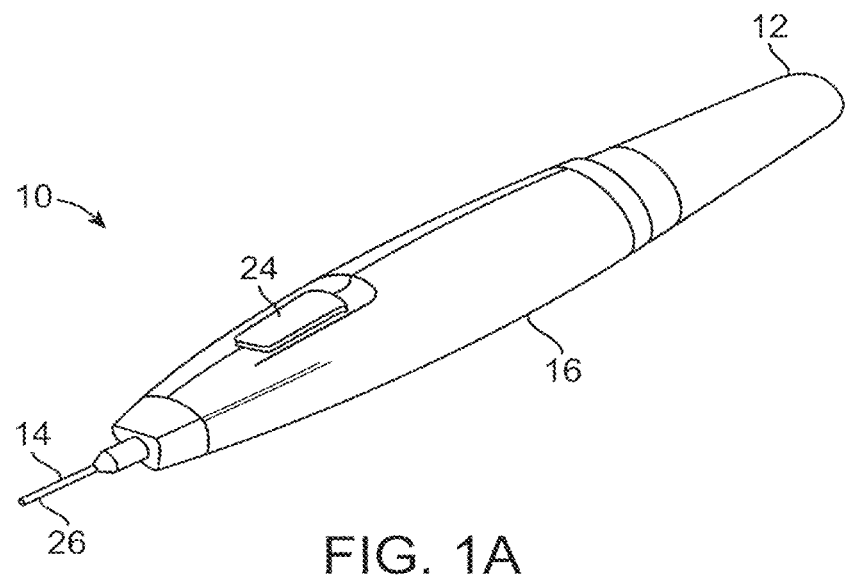
FIG. 1A is a perspective view of a self-contained subdermal cryogenic remodeling probe and system, according to an embodiment of the invention.

The present invention provides improved medical devices, systems, and methods. Embodiments of the invention will facilitate remodeling of target tissues disposed at and below the skin, optionally to treat a cosmetic defect, a lesion, a disease state, and/or so as to alter a shape of the overlying skin surface.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a permanent treatment that limits or avoids inflammation and mobilization of skeletal muscle satellite repair cells. In some embodiments, temporary axonotmesis degeneration of a motor nerve is desired, which may be induced using treatment temperatures from about −20° C. to about −100° C. and may be as low as −140° C. In some embodiments, neurotmesis injury of a motor nerve is desired, which may be induced using treatment temperatures below −140° C. and may be up to temperatures below −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", and U.S. patent application Ser. No. 13/325,004, entitled "Method for Reducing Hyperdynamic Facial Wrinkles", the full disclosures of which are each incorporated by reference herein.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms as disclosed in commonly assigned U.S. Pub. No. 2009/0248001 entitled "Pain Management Using Cryogenic Remodeling" the full disclosure of which is incorporated herein by reference.

Figure 1B:
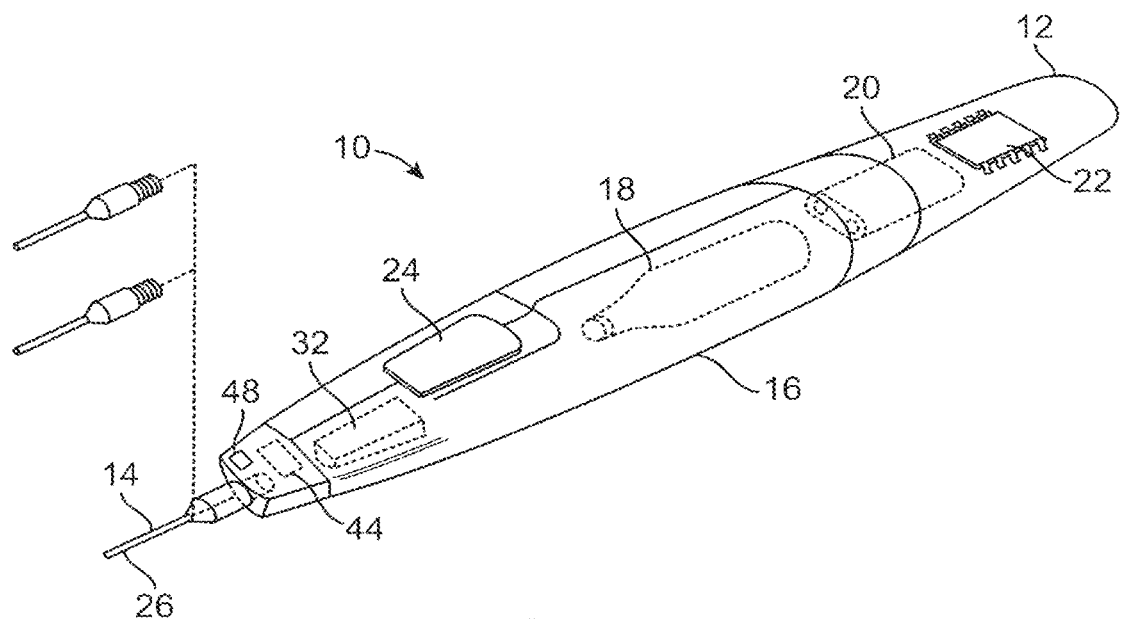
FIG. 1B is a partially transparent perspective view of the self-contained probe of FIG. 1A, showing internal components of the cryogenic remodeling system and schematically illustrating replacement treatment needles for use with the disposable probe, according to an embodiment of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 thereby helping to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 27 g needle having a sharpened distal end that is axially sealed. Probe 26 may have an axial length between distal end 14 of housing 16 and the distal end of the needle of between about 0.5 mm and 5 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 is releasably coupled with body 16 so that it may be replaced after use with a sharper needle (as indicated by the dotted line) or with a needle having a different configuration. In exemplary embodiments, the needle may be threaded into the body, it may be press fit into an aperture in the body or it may have a quick disconnect such as a detent mechanism for engaging the needle with the body. A quick disconnect with a check valve is advantageous since it permits decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature is also advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 comprises a canister, sometimes referred to herein as a cartridge, containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which is incorporated herein by reference.

The exemplary cooling fluid supply 18 comprises a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2:
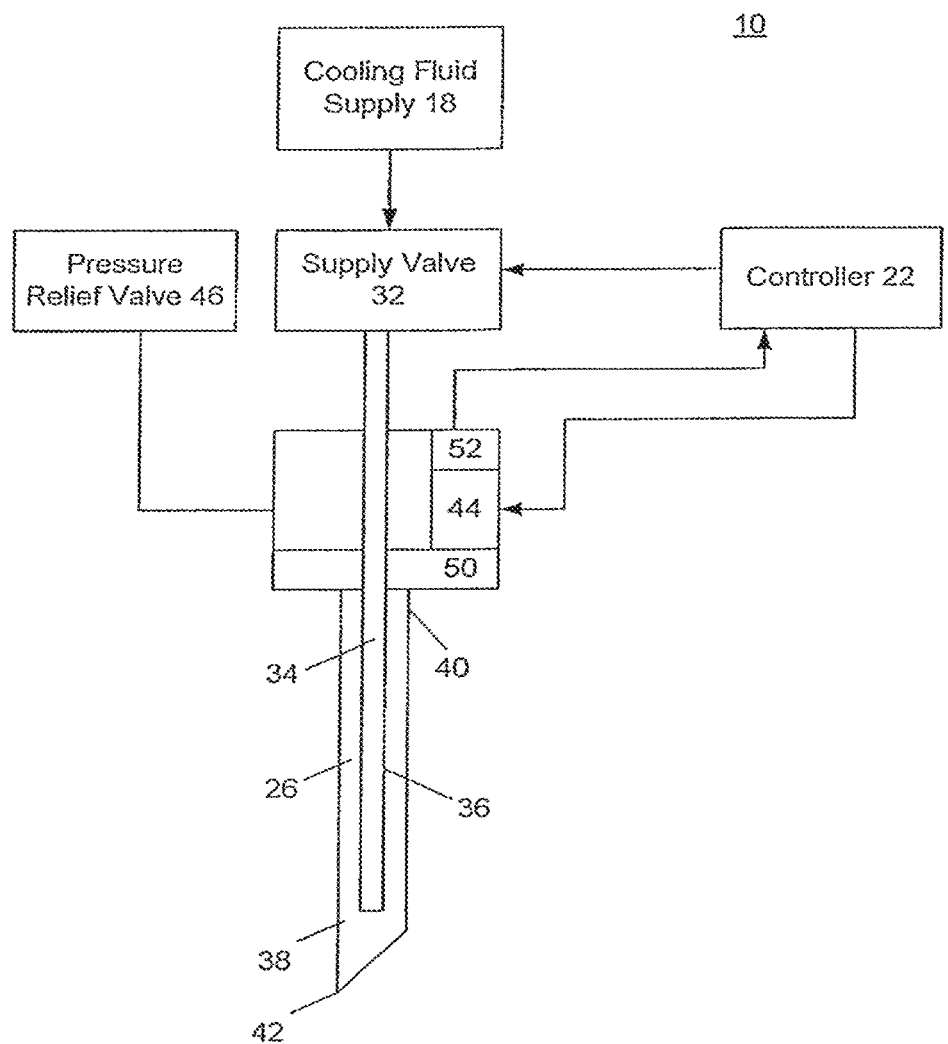
FIG. 2 schematically illustrates components that may be included in the treatment system, according to an embodiment of the invention.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2, an optional heater (not illustrated) may be used to heat cooling fluid supply 18 so that heated cooling fluid flows through valve 32 and through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Previously incorporated U.S. Patent Publication No. 2008/0200910 discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle 26 in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050, previously incorporated herein by reference. Thus, the relief valve allows better temperature control in the needle, minimizing transient temperatures. Further details on exhaust volume are disclosed in previously incorporated U.S. Pat. Pub. No. 2008/0200910.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 44 are placed in different positions within the thermally responsive element 50. In some embodiments, the second temperature sensor 53 is placed closer to a tissue contacting surface than the first temperature sensor is in order to provide comparative data (e.g., temperature differential) between the sensors. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e, fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154,254.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2, an optional cooling supply heater (not illustrated) may be used to heat cooling fluid supply 18 so that heated cooling fluid flows through valve 32 and through a lumen 34 of a cooling fluid supply tube 36. In some embodiments safety mechanism can be included so that the cooling supply is not overheated. Examples of such embodiments are disclosed in commonly assigned Int'l. Pub. No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 entitled "Dermal and Transdermal Cryogenic Microprobe Systems and Methods," the entire contents of which are incorporated herein by reference. U.S. Patent Pub. No. 2008/0200910, previously incorporated herein by reference, also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. Thus, the relief valve allows better temperature control in the needle, minimizing transient temperatures. Further details on exhaust volume are disclosed in U.S. Patent Publication No. 2008/0200910, previously incorporated herein by reference.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in U.S. Pub. No. 2008/0154254, previously incorporated herein by reference.

Figure 3A:
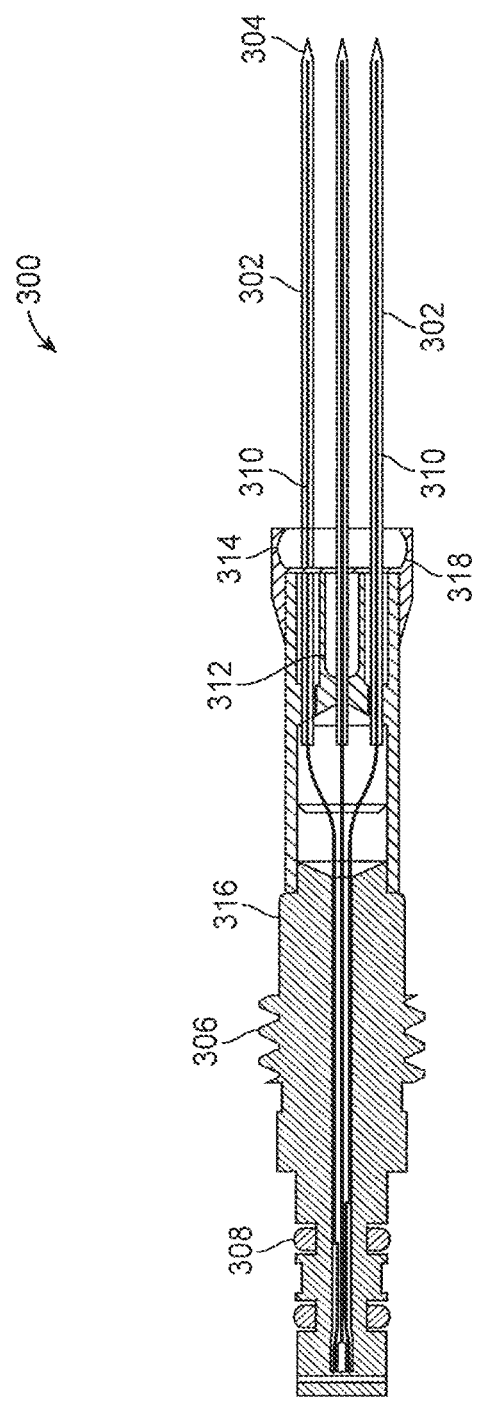
FIG. 3A-3D illustrate exemplary embodiments of a needle probe, according to embodiments of the invention.
Figure 3B:
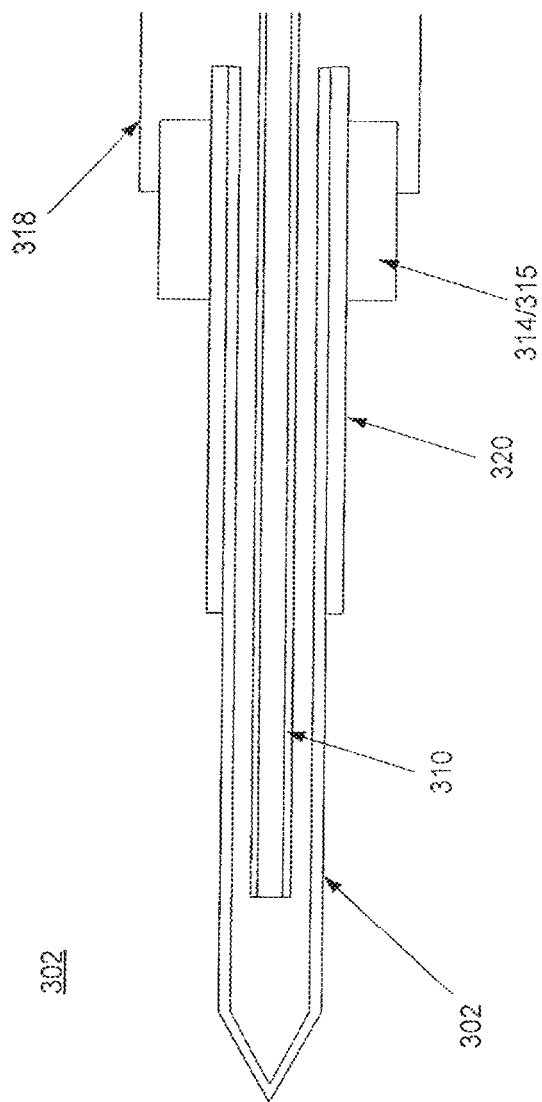

In the exemplary embodiment of FIG. 3A, probe tip 300 includes a resistive heater element 314 is disposed near the needle hub 318 and near a proximal region of needle shaft 302. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodelling for Cosmetic and Other Treatments", the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

A cladding 320 of conductive material is directly conductively coupled to the proximal portion of the shaft of needle shaft 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing heat to pressurized cryogenic cooling fluid passing within the proximal portion of the needle to affect complete vaporization of the fluid. Thus, the non-target tissue in contact with the proximal portion of the needle shaft 302 does not need to supply heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of a cooling zone to the distal portion of the needle shaft 302, which tends to demarcate at a distal end of the cladding 320. Accordingly, cooling zones are formed only about the distal portions of the needles—in this case to target a particular sensory nerve branch. Thus, while non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Figure 3C:
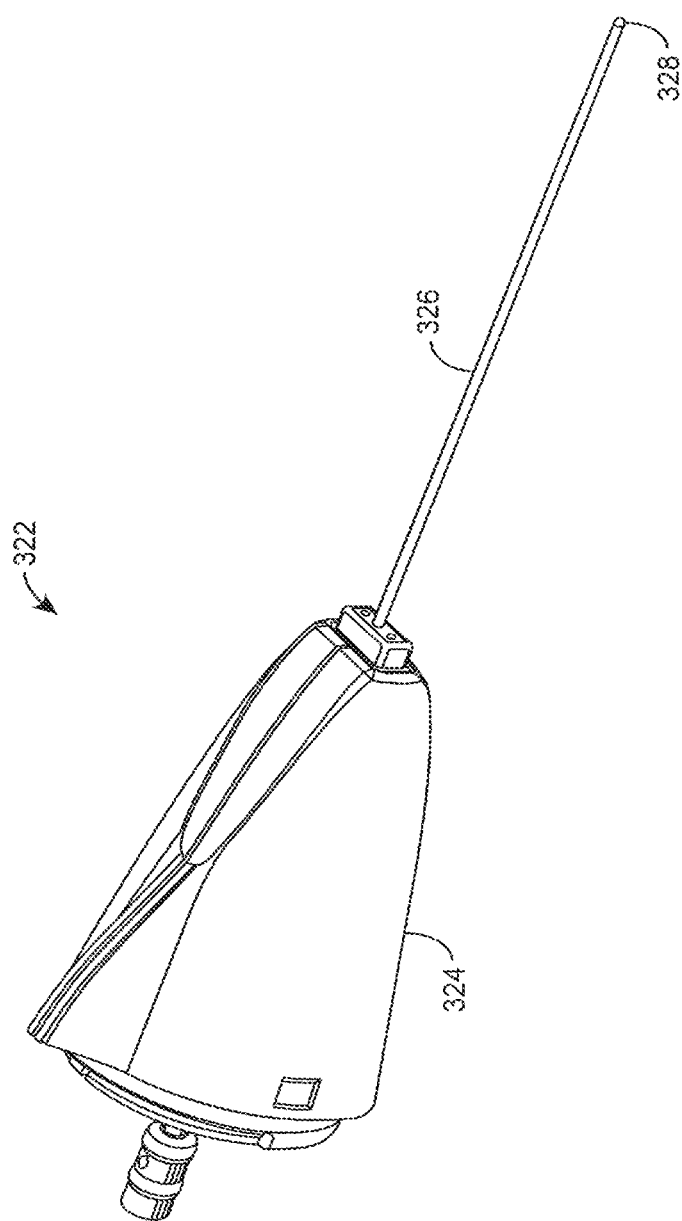
Figure 3D:
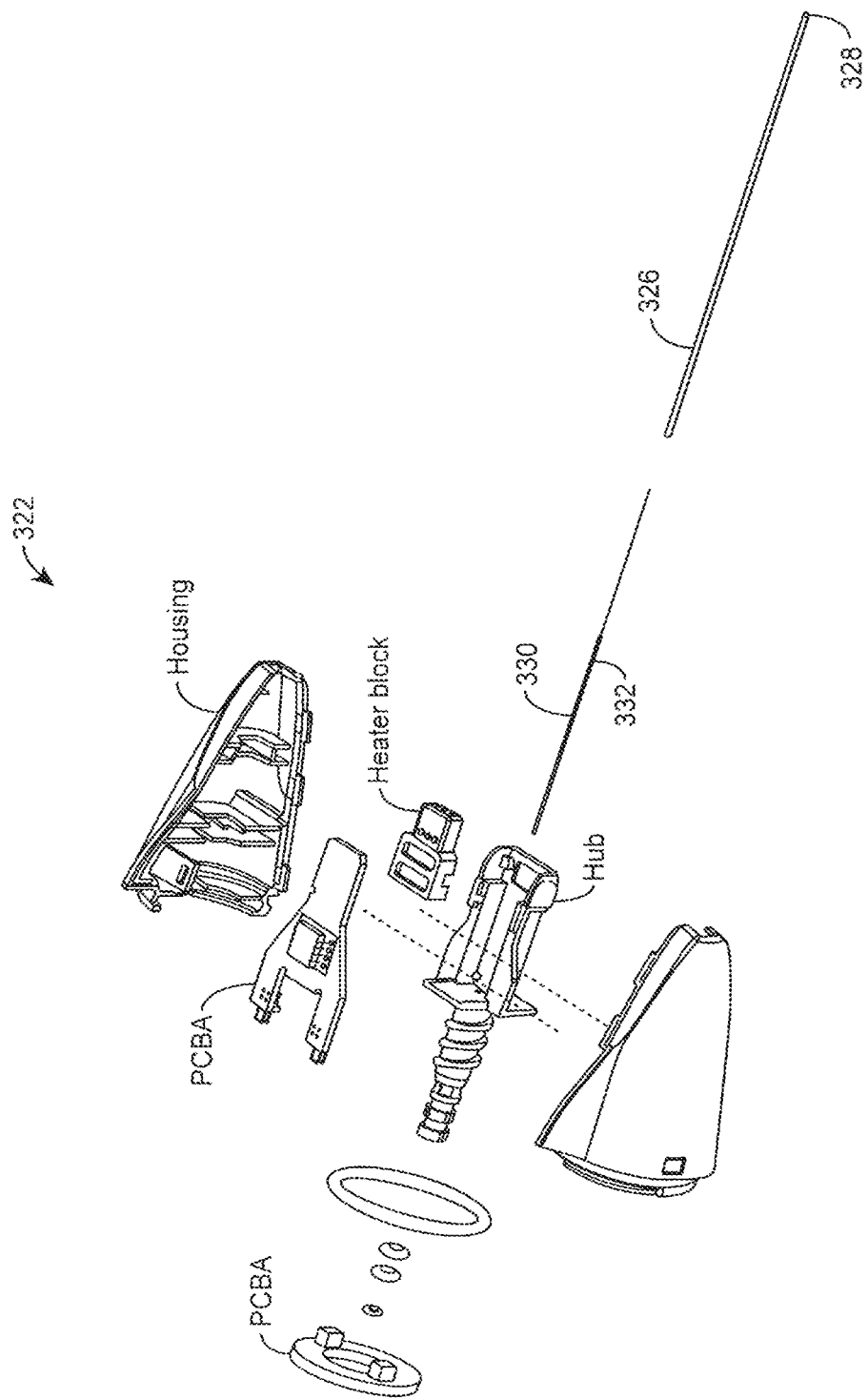

FIGS. 3C and 3D illustrates a detachable probe tip 322 having a hub connector 324 and an elongated probe 326. The probe tip 322 shares much of its construction with probe tip 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be greater than 20 gauge in size, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 are configured to resiliently bend in use, throughout their length at angles approaching 120°, with a 5-10 mm bend radius. This is very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility that others. The may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 are may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

In some embodiments, the probe tip 322 does not include a heating element, such as the heater described with reference to probe tip 300, since the effective treating portion of the elongated probe 324 (i.e., the area of the elongated probe where a cooling zone emanates from) is well laterally displaced from the hub connector 322 and elongated probe proximal junction. Embodiments of the supply tube are further described below and within commonly assigned U.S. Pub. No. 2012/0089211, which is incorporated by reference.

Figure 4A:
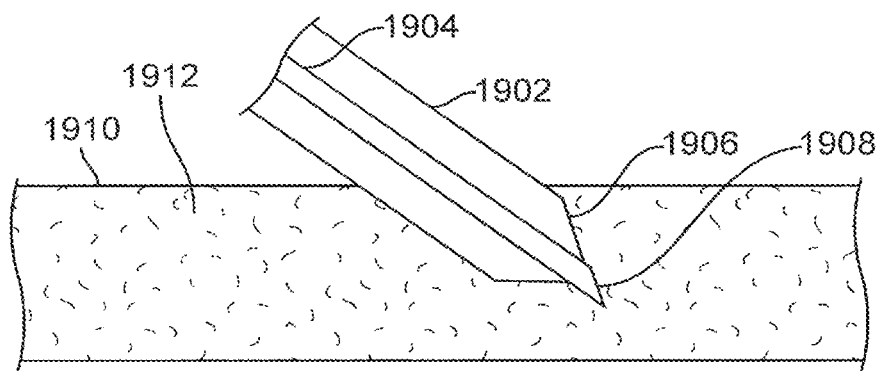
FIGS. 4A-4C illustrate an exemplary method of introducing a cryogenic probe to a treatment area, according to embodiments of the invention.
Figure 4B:
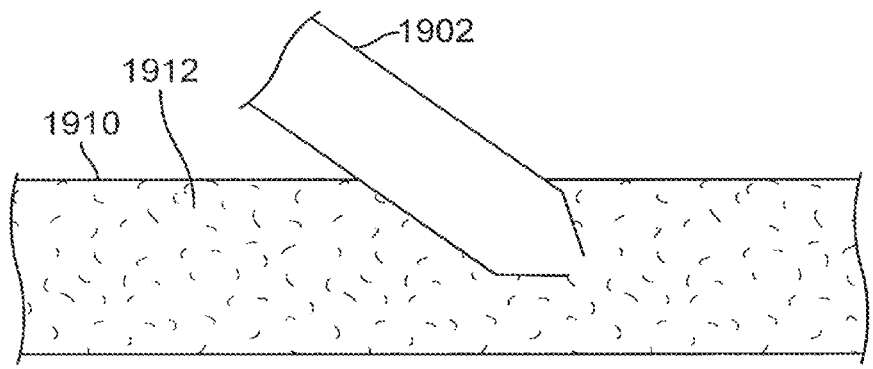
Figure 4C:
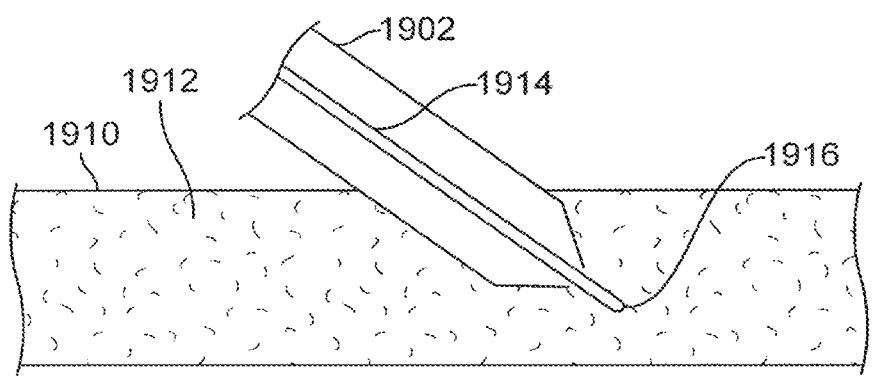

FIGS. 4A-4C illustrate an exemplary method of creating a hole through the skin that allows multiple insertions and positioning of a cryoprobe therethrough. In FIG. 4A a cannula or sheath 1902 is disposed over a needle 1904 having a tissue penetrating distal end 1908. The cannula may have a tapered distal portion 1906 to help spread and dilate the skin during insertion. The needle/sheath assembly is then advanced into and pierces the skin 1910 into the desired target tissue 1912. The inner pathway of the cannula or sheath 1902 may be curved to assist in directing the flexible needle 1904, or other probe, into a desired tissue layer coincident with the desired needle path in the tissue. Once the needle/sheath assembly has been advanced to a desired location, the needle 1904 may be proximally retracted and removed from the sheath 1902. The sheath now may be used as an easy way of introducing a cryoprobe through the skin without piercing it, and directing the cryoprobe to the desired target treatment area. FIG. 4B shows the sheath 1902 in position with the needle 1904 removed. FIG. 4C shows insertion of a cryoprobe 1914 into the sheath such that a blunt tip 1916 of the cryoprobe 1914 is adjacent the target treatment tissue. The cryoprobe may then be cooled and the treatment tissue cooled to achieve any of the cosmetic or therapeutic effects discussed above. In this embodiment, the cryoprobe preferably has a blunt tip 1916 in order to minimize tissue trauma. In other embodiments, the tip may be sharp and be adapted to penetrate tissue, or it may be round and spherical. The cryoprobe 1914 may then be at least partially retracted from the sheath 1902 and/or rotated and then re-advanced to the same or different depth and repositioned in sheath 1902 so that the tip engages a different portion of the target treatment tissue without requiring an addition piercing of the skin. The probe angle relative to the tissue may also be adjusted, and the cryoprobe may be advanced and retracted multiple times through the sheath so that the entire target tissue is cryogenically treated.

While the embodiment of FIGS. 4A-4C illustrate a cryoprobe having only a single probe, the cryoprobe may have an array of probes. Any of the cryoprobes described above may be used with an appropriately sized sheath. In some embodiments, the cryoprobe comprises a linear or two dimensional array of probes. Lidocaine or other local anesthetics may be used during insertion of the sheath or cryoprobe in order to minimize patient discomfort. The angle of insertion for the sheath may be anywhere from 0 to 180 degrees relative to the skin surface, and in specific embodiments is 15 to 45 degrees. The sheath may be inserted any depth, but in specific embodiments of treating lines/wrinkles of the face, the sheath may be inserted to a depth of 1 mm to 10 mm, and more preferably to a depth of 2 mm to 5 mm.

Figure 4D:
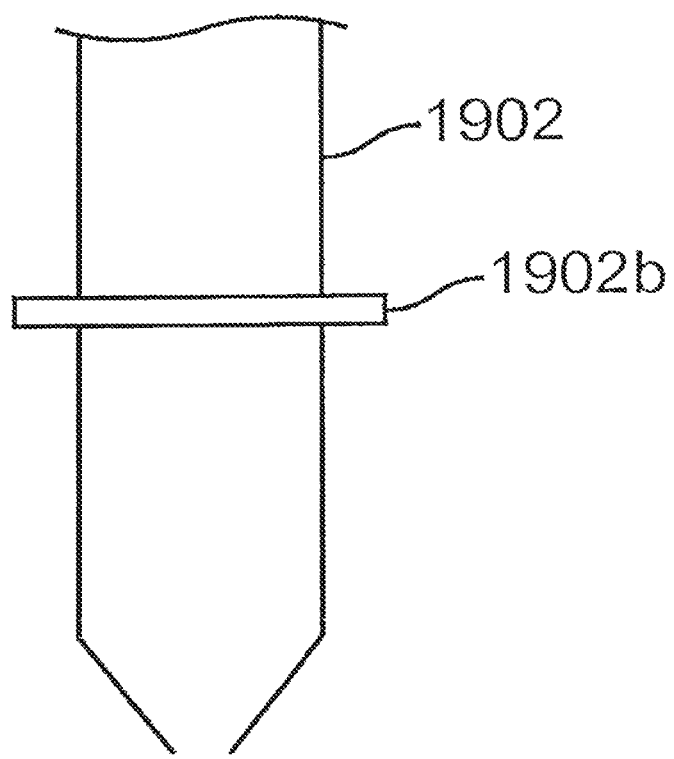
FIG. 4D illustrates an alternative embodiment of a sheath, according to an embodiment of the invention.

In an alternative embodiment seen in FIG. 4D, the sheath 1902 may include an annular flange 1902b on an outside surface of the sheath in order to serve as a stop so that the sheath is only inserted a preset amount into the tissue. The position of the flange 1902b may be adjustable or fixed. The proximal end of the sheath in this embodiment, or any of the other sheath embodiments may also include a one way valve such as a hemostasis valve to prevent backflow of blood or other fluids that may exit the sheath. The sheath may also insulate a portion of the cryoprobe and prevent or minimize cooling of unwanted regions of tissue.

Figure 5:
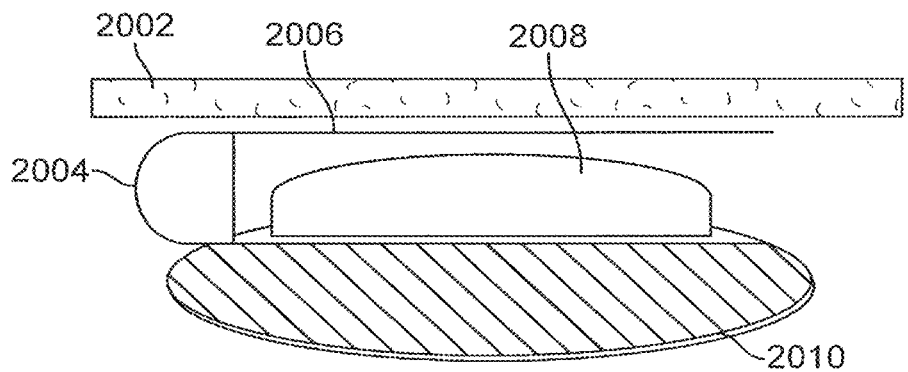
FIG. 5 illustrates an insulated cryoprobe, according to an embodiment of the invention.

Any of the cryoprobes described above may be used with the sheath embodiment described above (e.g. in FIGS. 3B, 4A-4C). Other cryoprobes may also be used with this sheath embodiment, or they may be used alone, in multi-probe arrays, or combined with other treatments. For example, a portion of the cryoprobe 2006 may be insulated as seen in FIG. 5. Cryoprobe 2006 includes a blunt tip 2004 with an insulated section 2008 of the probe. Thus, when the cryoprobe is disposed in the treatment tissue under the skin 2002 and cooled, the cryoprobe preferentially creates a cooling zone along one side while the other side remains uncooled, or only experiences limited cooling. For example, in FIG. 5, the cooling zone 2010 is limited to a region below the cryoprobe 2006, while the region above the cryoprobe and below the skin 2002 remain unaffected by the cooling.

Figure 6:
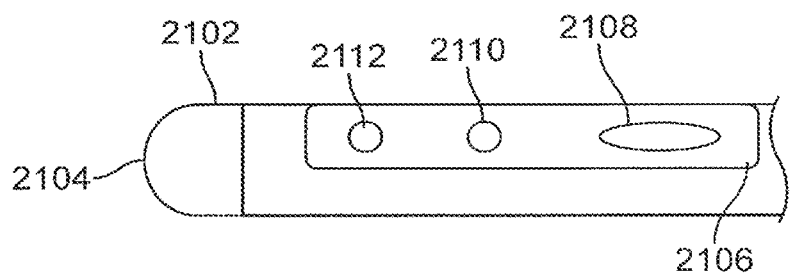
FIGS. 6-9 illustrate exemplary embodiments of cryofluid delivery tubes, according to embodiments of the invention.
Figure 7:
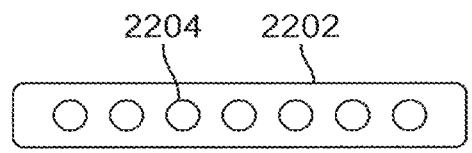
Figure 8:
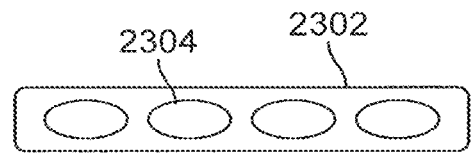
Figure 9:
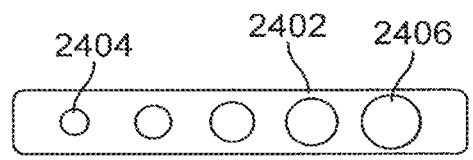

Different zones of cryotherapy may also be created by different geometries of the coolant fluid supply tube that is disposed in the cryoprobe. FIGS. 6-9 illustrate exemplary embodiments of different coolant fluid supply tubes. In FIG. 6 the coolant fluid supply tube 2106 is offset from the central axis of a cryoprobe 2102 having a blunt tip 2104. Additionally, the coolant fluid supply tube 2106 includes several exit ports for the coolant including circular ports 2110, 2112 near the distal end of the coolant fluid supply tube and an elliptical port 2108 proximal of the other ports. These ports may be arranged in varying sizes, and varying geometries in order to control the flow of cryofluid which in turn controls probe cooling of the target tissue. FIG. 7 illustrates an alternative embodiment of a coolant fluid supply tube 2202 having a plurality of circular ports 2204 for controlling cryofluid flow. FIG. 8 illustrates yet another embodiment of a coolant fluid supply tube 2302 having a plurality of elliptical holes, and FIG. 9 shows still another embodiment of a coolant fluid supply tube 2402 having a plurality of ports ranging from smaller diameter circular holes 2404 near the distal end of the supply tube 2402 to larger diameter circular holes 2406 that are more proximally located on the supply tube.

Figure 10:
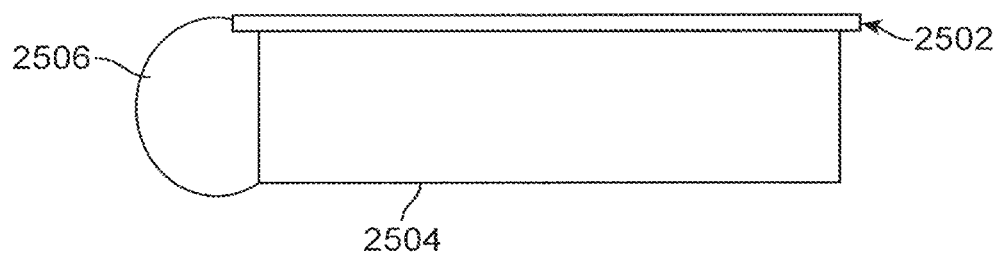
FIG. 10 illustrates an example of blunt tipped cryoprobe, according to an embodiment of the invention.

As discussed above, it may be preferable to have a blunt tip on the distal end of the cryoprobe in order to minimize tissue trauma. The blunt tip may be formed by rounding off the distal end of the probe, or a bladder or balloon 2506 may be placed on the distal portion of the probe 2504 as seen in FIG. 10. A filling tube or inflation lumen 2502 may be integral with or separate from the cryoprobe 2504, and may be used to deliver fluid to the balloon to fill the balloon 2506 up to form the atraumatic tip.

Figure 11:
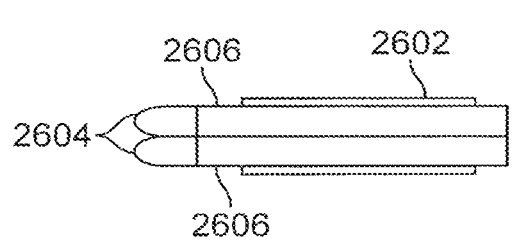
FIGS. 11 and 12 illustrate actuatable cryoprobes, according to embodiments of the invention.
Figure 12:
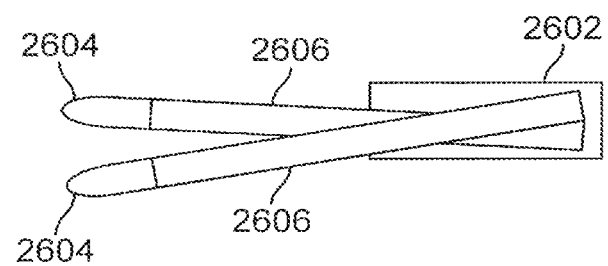

In some instances, it may be desirable to provide expandable cryoprobes that can treat different target tissues or accommodate different anatomies. For example, in FIGS. 11 and 12, a pair of cryoprobes 2606 with blunt tips 2604 may be delivered in parallel with one another and in a low profile through a sheath 2602 to the treatment area. Once delivered, the probes may be actuated to separate the tips 2604 from one another, thereby increasing the cooling zone. After the cryotherapy has been administered, the probes may be collapsed back into their low profile configuration, and retracted from the sheath.

In some embodiments, the probe may have a sharp tissue piercing distal tip, and in other embodiments, the probe may have a blunt tip for minimizing tissue trauma. To navigate through tissue, it may be desirable to have a certain column strength for the probe in order to avoid bending, buckling or splaying, especially when the probe comprises two or more probes in an array. One exemplary embodiment may utilize a variable stiff portion of a sleeve along the probe body to provide additional column strength for pushing the probe through tissue.

In many methods, the temporal branch of the facial nerve which feeds the frontalis, corrugator supercilii, and other facial muscles, the angular nerve, which enervates the corrugator supercilii and the procerus muscle, or nerves that enervate other facial muscles can be temporarily disrupted by applying cold therapy in anatomically based patterns in the temporal and other regions of the face. The disruption can be performed by using a cryoprobe that decreases the local environmental temperature sufficiently cold to induce a nerve block. The procedure can be designed to minimize patient discomfort through use of local anesthetics. Also the procedure can be performed simply with minimal discomfort and a short procedure time by targeting the treatment location with appropriate anatomical landmarks and designing the cryoprobe and cryotherapy to provide optimum treatment in minimum time.

In many embodiments, muscle contraction or pain can be eliminated by using a cryoprobe such as those previously described above to treat the nerve by identifying anatomical landmarks, measuring or applying a predetermined template to/from or between the identified landmarks, and laterally inserting a cryoprobe, bluntly dissecting tissue using the cryoprobe to reach the desired treatment location in a pattern that causes a sufficient number of local facial nerve branches in the target area to be impacted by the cryotreatment.

Figure 13A:
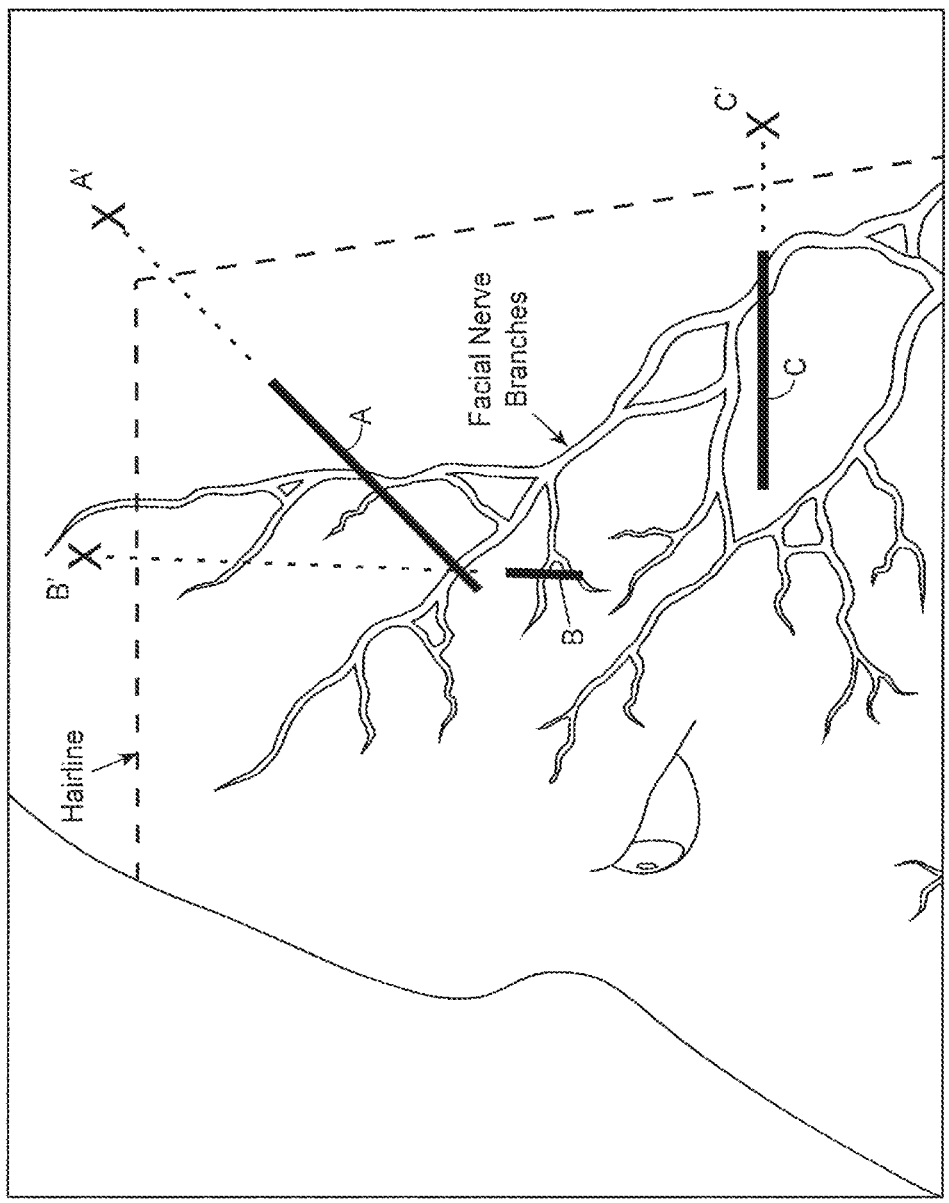
FIGS. 13A-13D illustrate methods for treating tissue, according to embodiments of the invention.

In some embodiments, a method comprises disruption the conduction a motor nerve in order to minimize the appearance of hyperdynamic facial wrinkles in the forehead, frown, crow's feet and other areas of the face. Three examples of diagonal, vertical, and horizontal treatments, respectively, portions A, B, and C, lying across portions of the temporal branch of a facial nerve (TB-FN) are illustrated in FIG. 13A. The treatment of horizontal forehead wrinkles may be initiated by creating an incision point beyond the hair line, marked as X, here shown as points A', B', and C'. In this manner, any temporary scarring caused by exposure to cold or otherwise is hidden from view. The cryogenic needle probe array is then inserted into the tissue. In some embodiments, a sheath can be used as shown in FIGS. 4A-4C, however this is not required. Generally, the incision point is laterally displaced from the area of treatment, with respect to the surface of the skin. In terms of landmarks, the incision point is generally at the scalp in a region covered by hair, i.e., beyond the hairline (e.g., 1-10 mm), in some cases well beyond the hairline (e.g., >10 mm), while the treatment area is underneath a visible portion of the skin.

In some embodiments, the cryogenic probe can be inserted through the skin after an incision is made and then advanced through softer tissue layers such as fat, muscle or other soft tissue, until a resilient tissue layer or structure is encountered, for example, such as a fascial layer, cartilage, periosteum, or bone. The resilient nature of the tissue layer prevents puncture by a blunt instrument, such as the cryogenic probe. The tip of the probe can interface with force against the resilient tissue layer, and then flex along the resilient tissue layer without piercing, and be advanced there along in a gliding movement until its distal tip is in close proximity to a target nerve found in close proximity to a tough protective structure. The nerve can then be cryogenically treated to create a cosmetically beneficial effect such as the alleviation of wrinkles or to mitigate pain in the case of a sensory nerve.

Skin tissue, including facial tissue, includes many layers. In simplistic terms, between skin and muscle lies a layer of subcutaneous tissue, a layer of temporoparietal fascia (TPF), loose areolar tissue, and then deep temporoparietal fascia (sDTF). For the purposes of this disclosure, tissue layers between the subcutaneous tissue and muscle will be referred to as the TPF-sDTF layer, or simply TPF-sDTF. Nerves of interest for treatment are generally positioned within the TPF-sDTF, and/or directly adjacent, i.e., between the TPF-sDTF and subcutaneous tissue depending on the specific location of the nerve. For example, the TB-FN extends along a portion of the TPF-sDTF layer. The point of incision is generally made so that the TPF-sDTF is accessible.

With attention back to FIG. 13A, after an incision is made, a cryogenic probe in inserted into the point of incision, to the depth of the TPF-sDTF, but not past the sDTF. The cryogenic probe includes a distal tip extending from an elongated body. For example, the cryogenic probe tip disclosed in FIGS. 3C and 3D can be used. After insertion, the TPF is then bluntly dissected by applying physical force to the cryogenic probe, to move the elongated body along treatment vectors, shown here as dotted lines. Often, movement of the elongated body is visible underneath the skin, thereby enabling positioning of the treating portion to a particular area. It should be understood that the blunt tip and flexibility of the cryogenic probe enable it to dissect the TPF while gliding over the sDTF within the TPF-sDTF layer. This is both a safety and ease-of-use advantage, since piercing the sDTF is very unlikely due to the blunt tip. Accordingly, the portion of the elongated probe body within the TPF-sDTF self-aligns to be substantially parallel to the TPF-sDTF, since it is physically confined between the sDTF and the upper subcutaneous tissue. Placement of the blunt tip can be aided by external palpation to encourage the tip to dissect along convex or concave surfaces and remain within the desired tissue layer.

Figure 13B:
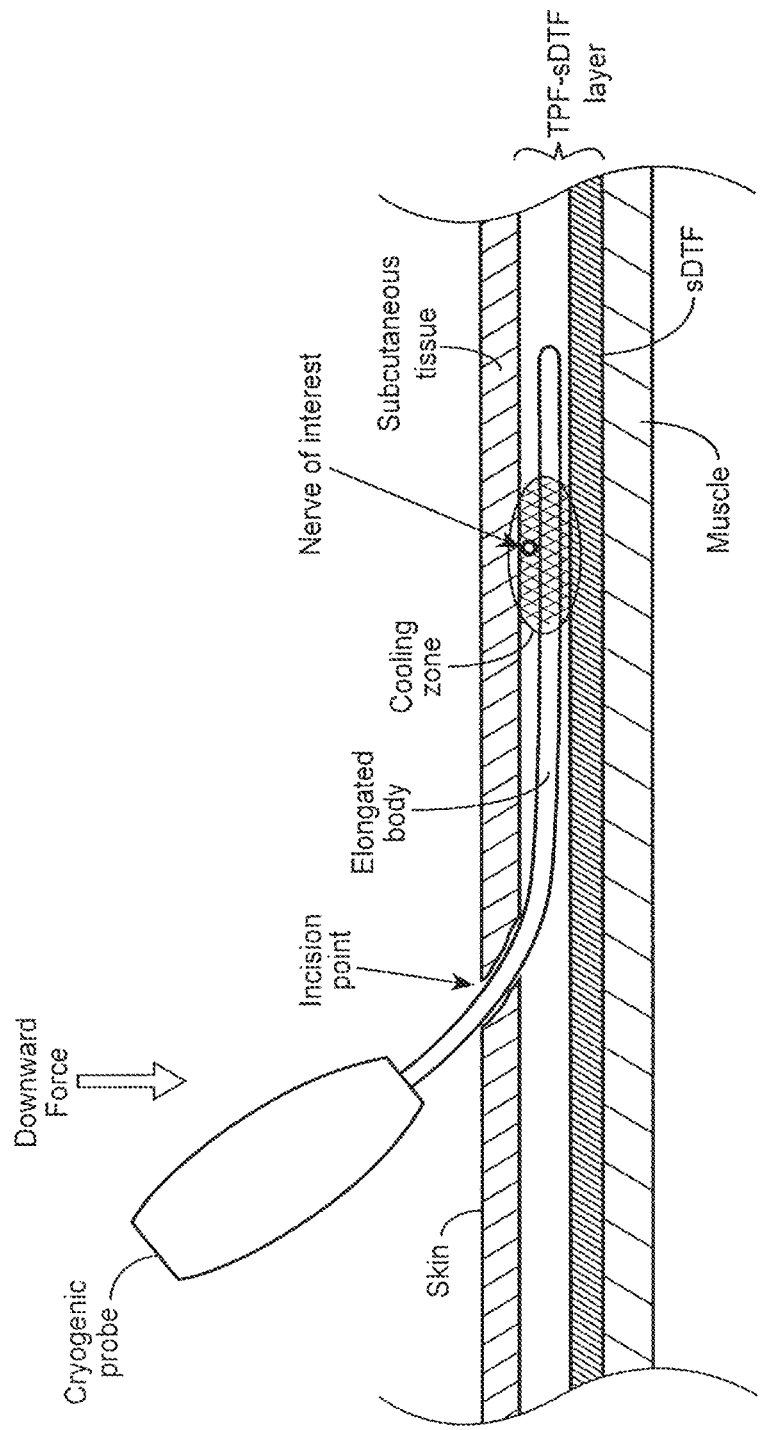

The cryogenic probe dissects the TPF until a treating portion of the cryogenic probe is directly adjacent to a treatment portion (e.g., A, B, and C) of a target nerve, such as the TB-FN, as illustrated in FIG. 13B. The treating portion of the cryogenic probe is a distinct portion along the elongated body where a cooling zone emanates from, typically the exit point(s) of an internal supply tube. In some embodiments the distal tip is the treating portion of the cryogenic probe, while in other embodiments a mid-portion of the elongated body is the treating portion. As shown, a downward force is applied to the handle of the cryogen probe to longitudinally move the elongated body within the TPF-sDTF. This is possible due to the self-aligning tendency of the probe within the TPF-sDTF. Thus, the downward force results in forward movement along the longitudinal axis of the elongated body. When applying the downward force, the elongated body can be bent without rupturing the elongated body or supply tube, due to the resilient nature of the probe.

Once the cryogenic probe is positioned, it may be activated to generate a cooling zone by flowing a cryogenic fluid through the elongated body, as well described above. The cryogenic probe is held in place until the desired treatment at the treatment zone is achieved. The cryogenic probe can then be removed from the body, or repositioned for additional treatment as further discussed below. Such methods are advantageous because they help mitigate visible temporary scaring (i.e, redness, scabs, blackening) that may occur with use of cryogenic needles, since the point of incision can be hidden by hair. Also, often only one point of entry is required, thus greatly reducing the quantity of any temporary scars. Further, the method mitigates issues associated with nerve depth variability, which can be the case when approaching from directly above the treatment portion with a piercing cryogenic needle, since the target nerve is within the TPF-sDTF that the elongated body travels within.

Figure 13C:
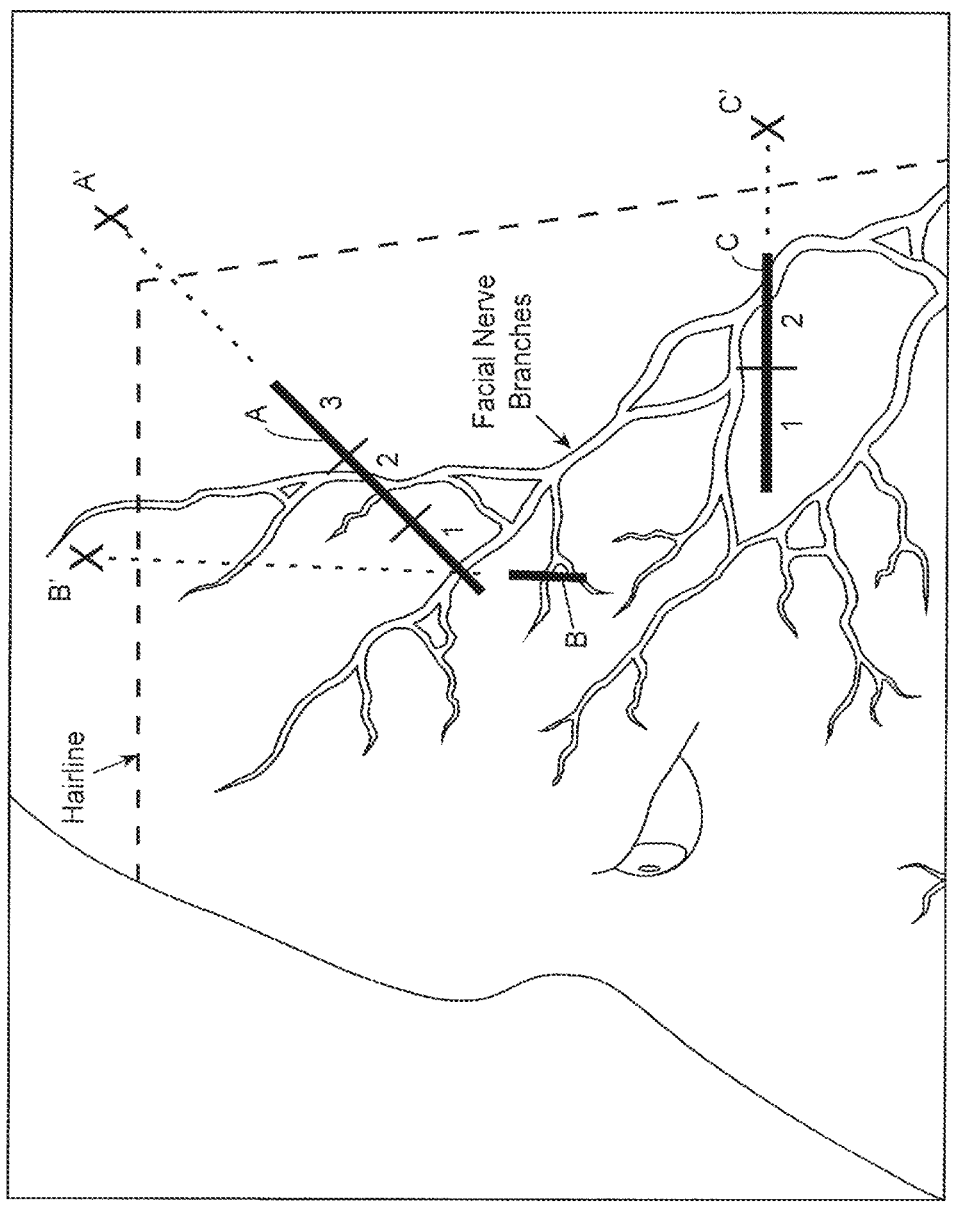
Figure 13D:
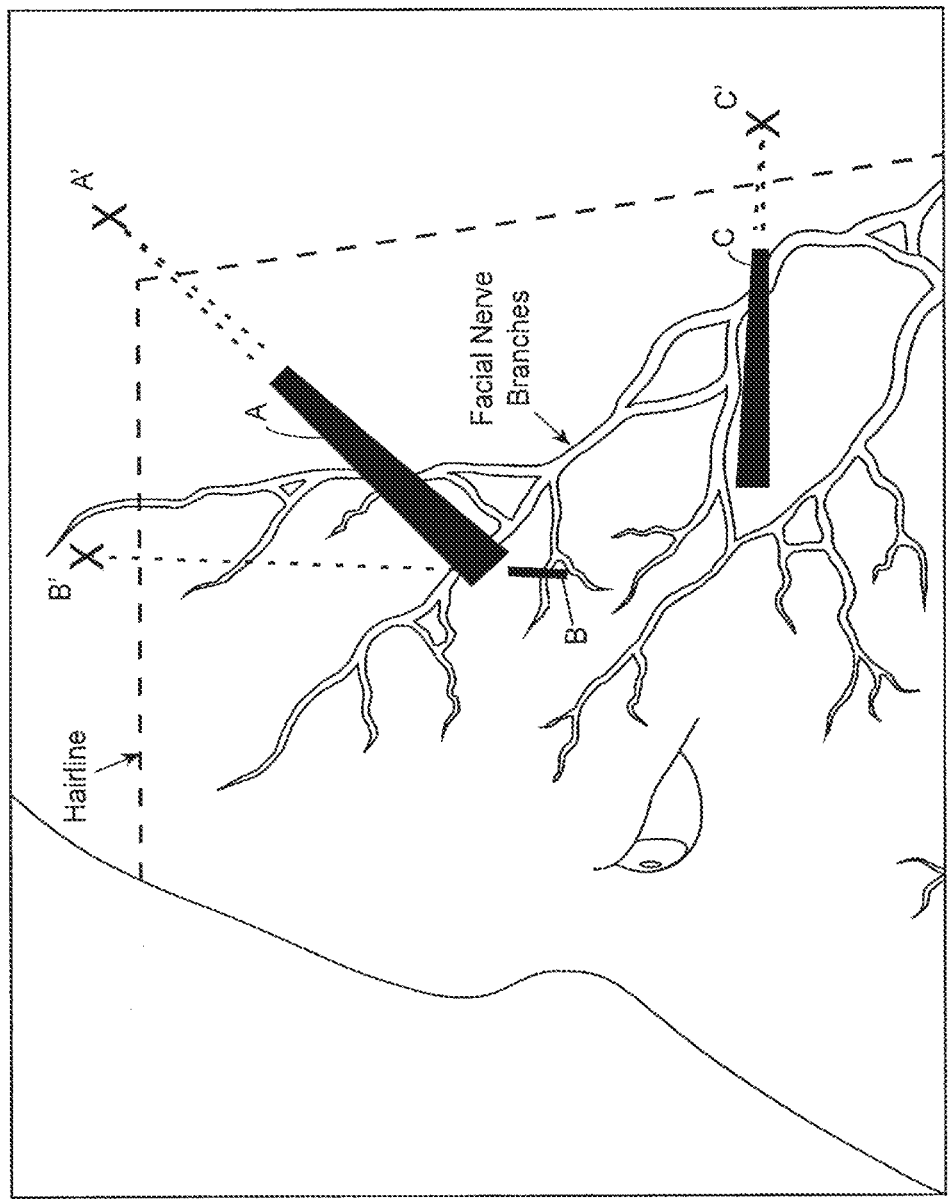

As mentioned above, it may be desirable to create more than one treatment zone to affect a nerve or cluster of nerves as depicted in FIGS. 13C and 13D. In FIG. 13C, a plurality of treatment zones have been created along treatments portions A and C to create a treatment "fence". This may be achieved by linearly withdrawing or advancing the cryogenic probe after a treatment is first performed, and then repeating the treatment at the new location. As shown, three treatment zones have been created along treatment portion A, and two treatments zones have been created along treatment portion C, however, more treatment zones than shown can be created. The treatment zones may be spatially separated by some desired distance, lay end-to-end, or overlap.

An alternative treatment pattern is depicted in FIG. 13D. Here, the cryoprobe has been adjusted angularly about the incision point after an initial treatment zone has been created, and then used for retreatment, thus creating a treatment "plane". Generally at least two treatment zones are required to create a plane, and more may be generated as well. As shown, treatment plane has been created at treatment portions A and C by performing a plurality of angularly separated treatments at each portion. As with respect to the method shown in FIG. 13C, treatment zones for creating a treatment plane may be spatially separated by some desired distance, lay side-by-side, or overlap. In some embodiments, the cryoprobe is actuatable, such as the probes shown in FIGS. 11 and 12, and thus actuation of the probes can be performed instead of angular displacement.

While the exemplary embodiments have been described in some detail for clarity of understanding and by way of example, a number of modifications, changes, and adaptations may be implemented and/or will be obvious to those as skilled in the art. For example, while treatment of a motor nerve is demonstrated in FIGS. 13C and 13D, the exemplary methods and devices disclosed herein are also useable in treating any nerve including peripheral nerves which will include sensory nerves.

Further, treatment is not limited to facial tissue, since the interfaces separating two tissues (e.g. bone, muscle, and organ) including fascia layers are found throughout the body and can be used to guide treatment of target nerves. Devices and method for pain management are disclosed herein as Appendix A, which consists of U.S. Provisional Application No. 61/800,478, which is incorporated by reference. Thus, the devices disclosed herein, such as the one shown in FIGS. 3C and 3D, can be used to treat sensory nerves disclosed in Appendix A. For example, the device of FIGS. 3C and 3D can be used to dissect fascia along the first and/or second lines of the treatment zone depicted in FIG. 6 of Appendix A, and thus treat sensory nerves that intersect with the treatment zone.

Further, the devices, systems, and methods can be used for management of movement disorders, for example such as: Akathisia, Akinesia Associated Movements (Mirror Movements or Homolateral Synkinesis), Athetosis (contorted torsion or twisting), Ataxia (gross lack of coordination of muscle movements), Ballismus (violent involuntary rapid and irregular movements), Hemiballismus (affecting only one side of the body), Bradykinesia (slow movement), Cerebral palsy, Chorea (rapid, involuntary movement), Sydenham's chorea, Rheumatic chorea, Huntington's disease, Dystonia (sustained torsion), Dystonia muscularum, Blepharospasm, Writer's cramp, Spasmodic torticollis (twisting of head and neck), Dopamine-responsive dystonia (hereditary progressive dystonia with diurnal fluctuation or Segawa's disease), Geniospasm (episodic involuntary up and down movements of the chin and lower lip), Myoclonus (brief, involuntary twitching of a muscle or a group of muscles), Metabolic General Unwellness Movement Syndrome (MGUMS), Mirror movement disorder (involuntary movements on one side of the body mirroring voluntary movements of the other side), Parkinson's disease, Paroxysmal kinesigenic dyskinesia, Restless Legs Syndrome RLS (WittMaack-Ekboms disease), Spasms (contractions), Stereotypic movement disorder, Stereotypy (repetition), Tardive dyskinesia, Tic disorders (involuntary, compulsive, repetitive, stereotyped), Tourette's syndrome, Tremor (oscillations), and Wilson's disease. It is believed that treatment of nerves associated with such movement disorders using the methods and systems disclosed herein can be beneficial. Hence, the scope of the present invention is limited solely by the independent claims.

What is claimed is:

1. A method for cryogenically treating a nerve of a patient, the method comprising:
   creating an access site within tissue laterally displaced from a nerve, the tissue comprising skin, a layer of soft tissue and a layer of resilient tissue,
   inserting a cryogenic probe having a cryogenic treating portion and a blunt distal tip extending from an elongated body into the access site, wherein the cryogenic probe includes a supply tube extending within the elongated body from a proximal end of the elongated body to the cryogenic treating portion;
   bluntly dissecting the layer of soft tissue using the cryogenic probe such that the cryogenic treating portion of the cryogenic probe is directly adjacent to the layer of resilient tissue;
   advancing the cryogenic probe such that the elongated body of the cryogenic probe laterally traverses along the layer of resilient tissue to position the cryogenic treating portion at a location adjacent to the nerve; and
   activating the cryogenic treating portion to generate a treatment zone at the location to cause a therapeutic effect in the nerve.

2. The method of claim 1, wherein the elongated body and supply tube are configured to resiliently bend.

3. The method of claim 1, further comprising deflecting the blunt distal tip of the cryogenic probe against the layer of resilient tissue.

4. The method of claim 1, further comprising bending a portion of the elongated body of the cryogenic probe prior to inserting the cryogenic probe into the access site.

5. The method of claim 1, wherein a portion of the elongated body is configured to self-align within the layer of soft tissue to be substantially parallel with the layer of resilient tissue as it laterally traverses along the layer of resilient tissue.

6. The method of claim 1, wherein the layer of soft tissue is comprised of adipose tissue, subcutaneous tissue, and/or muscle.

7. The method of claim 1, wherein the layer of resilient tissue is a fascia layer.

8. The method of claim 1, wherein the layer of resilient tissue is cartilage, periosteum, or bone.

9. The method of claim 1, wherein the tissue comprises muscle under the layer of resilient tissue and wherein the layer of resilient tissue comprises a tissue interface separating the muscle and the layer of soft tissue.

10. The method of claim 1, further comprising repeatedly moving and activating the cryogenic treating portion of the cryogenic probe such that a plurality of treatment zones is created across the nerve adjacent to the layer of resilient tissue and wherein moving the cryogenic treating portion comprises linearly withdrawing or advancing the cryogenic probe along the layer of resilient tissue.

11. The method of claim 1, wherein the nerve is the temporal branch of a facial nerve.

12. The method of claim 1, wherein the layer of soft tissue is a layer of temporoparietal fascia (TPF).

13. The method of claim 1, wherein the layer of resilient tissue is a layer of deep temporoparietal fascia (sDTF).

14. The method of claim 1, wherein the nerve is a sensory nerve.

15. The method of claim 1, wherein the nerve is a motor nerve.

16. The method of claim 15, wherein the treatment zone is cooled to a temperature of below about −20 degrees C.

17. The method of claim 15, wherein the treatment zone is cooled to a temperature of below about −100 degrees C.

18. A method for cryogenically treating a nerve of a patient, the method comprising:
creating an access site within tissue laterally displaced from a nerve, the tissue comprising skin, a layer of soft tissue layer and a layer of resilient tissue,
inserting a cryogenic probe having a cryogenic treating portion and a blunt distal tip extending from an elongated body into the access site, wherein the cryogenic probe includes a supply tube extending within the elongated body from a proximal end of the elongated body to the cryogenic treating portion;
bluntly dissecting the layer of soft tissue using the cryogenic probe such that the cryogenic treating portion of the cryogenic probe is directly adjacent to the layer of resilient tissue;
advancing the cryogenic probe such that the elongated body of the cryogenic probe laterally traverses along the layer of resilient tissue to position the cryogenic treating portion at a first location adjacent to the nerve;
activating the cryogenic treating portion to generate a first treatment zone at the first location to cause a therapeutic effect in the nerve; and
relocating the treating portion of the cryogenic probe to a second location
and activating the cryogenic treating portion to generate a second treatment zone at the second location to further the therapeutic effect.

19. The method of claim 18, wherein the treating portion of the cryogenic
probe is relocated to the second location without withdrawing the treating portion from the access site.

20. The method of claim 18, wherein the second treatment zone is adjacent to the first treatment zone.

21. The method of claim 18, wherein the second treatment zone overlaps with the first treatment zone.

22. The method of claim 18, wherein the treatment zones comprise a treatment fence across the nerve.

23. The method of claim 18, wherein the treatment zones comprise a treatment plane across the nerve.

24. The method of claim 18, wherein the treatment zones are spatially separated from each other.

25. The method of claim 18, wherein the layer of soft tissue is comprised of adipose tissue, subcutaneous tissue, and/or muscle.

26. The method of claim 18, wherein the layer of resilient tissue is a fascia layer.

27. The method of claim 18, wherein the layer of resilient tissue is cartilage, periosteum, or bone.

28. The method of claim 18, wherein the tissue comprises muscle under the layer of resilient tissue and wherein the layer of resilient tissue comprises a tissue interface separating the muscle and the layer of soft tissue.

29. The method of claim 18, wherein the nerve is the temporal branch of a facial nerve.

30. The method of claim 18, wherein the layer of soft tissue is a layer of temporoparietal fascia (TPF).

31. The method of claim 18, wherein the layer of resilient tissue is a layer of deep temporoparietal fascia (sDTF).

32. The method of claim 18, wherein the nerve is a sensory nerve.

33. The method of claim 18, wherein the nerve is a motor nerve.

34. The method of claim 33, wherein the treatment zone is cooled to a temperature of below about −20 degrees C.

35. The method of claim 33, wherein the treatment zone is cooled to a temperature of below about −100 degrees C.

* * * * *